United States Patent
Lee et al.

(10) Patent No.: US 9,170,234 B2
(45) Date of Patent: Oct. 27, 2015

(54) MAGNETIC SENSOR ARRAY AND APPARATUS FOR DETECTING DEFECT USING THE MAGNETIC SENSOR ARRAY

(75) Inventors: Jin-Yi Lee, Gwangju (KR); Jong-Woo Jun, Busan (KR); Ji-Seong Hwang, Jeollanam-do (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 1075 days.

(21) Appl. No.: 12/447,907
(22) PCT Filed: Aug. 7, 2007
(86) PCT No.: PCT/KR2007/003801
§ 371 (c)(1),
(2), (4) Date: Apr. 30, 2009
(87) PCT Pub. No.: WO2008/054056
PCT Pub. Date: May 8, 2008

(65) Prior Publication Data
US 2010/0042336 A1     Feb. 18, 2010

(30) Foreign Application Priority Data
Nov. 1, 2006 (KR) .................. 10-2006-0107338

(51) Int. Cl.
*G01N 27/82* (2006.01)
*G01N 27/90* (2006.01)
(52) U.S. Cl.
CPC ................. *G01N 27/9006* (2013.01)
(58) Field of Classification Search
CPC ..... G01N 27/82; G01N 27/825; G01N 27/83; G01N 27/87; G01N 27/90; G01N 27/9006; G01N 27/9013; G01N 27/902; G01N 27/9026; G01N 27/9033; G01N 27/904; G01N 27/9046; G01R 33/0005; G01R 33/0011; G01R 33/0094; G01R 33/02; G01R 33/04; G01R 33/06; G01R 33/12; G01R 33/1215; G01R 33/1223; G01R 33/1253

USPC ........................................... 324/238
See application file for complete search history.

(56) References Cited

U.S. PATENT DOCUMENTS 5,969,521 A * 10/1999 Kurita et al. ................ 324/229
6,057,684 A    5/2000 Murakami et al.
(Continued)

OTHER PUBLICATIONS

Jinyi Lee et al; "Numerical Analysis of Magneto-Optical Eddy Current Imaging Using FEM", Key Engineering Materials, vols. 321-323, pp. 1451-1456, Oct. 2006.
(Continued)

*Primary Examiner* — Jay Patidar
*Assistant Examiner* — David M. Schindler
(74) *Attorney, Agent, or Firm* — Ladas & Parry LLP

(57) ABSTRACT

If surface defects, near surface defects, or internal defects of a ferromagnetic substance object, a paramagnetic substance object, or a mixture object of ferromagnetic and paramagnetic substances are not quantitatively analyzed, the detected results can be differently analyzed depending on the knowledge or skill of an inspector. A defect detection apparatus according to an exemplary embodiment of the present invention includes an induced current applier, a magneto-electric converter, a signal processor, a signal converter, and a data processor. The induced current applier applies a line or surface current to an object that is to be measured by using an alternating current (AC) having a frequency varying depending on a depth to be measured. The magneto-electric converter senses a magnetic field generated from the object by the Hn e or surface current and generates a magnetic field sensing signal corresponding to a strength of the sensed magnetic field. The signal processor filters and amplifies the magnetic field sensing signal and outputs a signal corresponding to amplitude of the filtered and amplified signal. The signal converter converts the signal output from the signal processor into a digital signal. The data processor quantitatively converts an intensity of a magnetic field generated from the object into a numerical value based on the digital signal output from the signal converter.

14 Claims, 21 Drawing Sheets

(56) References Cited

U.S. PATENT DOCUMENTS

| | | | |
|---|---|---|---|
| 6,150,809 A | | 11/2000 | Tiernan |
| 6,636,037 B1 | | 10/2003 | Ou-Yang |
| 6,720,775 B2 | | 4/2004 | Plotnikov |
| 6,774,627 B2 | | 8/2004 | Yokota |
| 7,084,623 B2 | | 8/2006 | Imamoto |
| 7,495,433 B2 | * | 2/2009 | Daalmans et al. ............ 324/238 |
| 7,902,820 B2 | * | 3/2011 | Vervaeke et al. ............ 324/251 |
| 2003/0210040 A1 | * | 11/2003 | Kang et al. .................... 324/228 |
| 2005/0122099 A1 | | 6/2005 | Imamoto et al. |
| 2005/0127908 A1 | * | 6/2005 | Schlicker et al. ............ 324/240 |
| 2005/0258828 A1 | * | 11/2005 | Johnson et al. ............... 324/251 |
| 2009/0139335 A1 | * | 6/2009 | Kroning et al. ................ 73/597 |

OTHER PUBLICATIONS

Jinyi Lee, et al; "A Study of Leakage Magnetic Flux Detector using Hall Sensors Array", Key Engineering Materials vols. 306-308, pp. 235-240; Mar. 2006.

Haiyan Sun, et al; "Enhanced Flaw Detection Using an Eddy Current Probe with a Linear Array of Hall Sensors", AIP Conference Proceedings; vol. 760, issue 1, pp. 516-522, Apr. 2005.

European Search Report; dated Mar. 5, 2012; Appln. No. 07793409. 9-2204 / 2084524; PCT/KR2007003801.

EPO Office Action date Aug. 19, 2013; Appln. No. 07 793 409.9-1554.

* cited by examiner

MAGNETIC SENSOR ARRAY AND APPARATUS FOR DETECTING DEFECT USING THE MAGNETIC SENSOR ARRAY

TECHNICAL FIELD

The present invention relates to a magnetic sensor array and an apparatus for detecting defects of a ferromagnetic structure, a paramagnetic structure, and a structure formed of ferromagnetic and paramagnetic substances using the magnetic sensor array.

BACKGROUND ART

A non-destructive inspection method using a magnetic phenomenon is useful to detect a surface defect of a structure, a near surface defect of the structure, or an internal defect of the structure. The non-destructive inspection method can be used to detect a defect of a large plant or structure used for nuclear power generation, a thermal power plant, chemical industry, etc.

A paramagnetic substance, such as an aluminum alloy or stainless steel, is used for airplanes or nuclear power generation equipment. A non-destructive inspection method using magneto-optical effects has attracted attention as a method of measuring damage to a paramagnetic substance. In particular, a Magneto-Optical eddy current Imager (MOI) has been developed by PRI R&D Co. to non-destructively detect the defects of an airplane. An image indicating a surface fatigue crack and erosion of a paramagnetic substance, a defect of a near surface of the paramagnetic substance, etc., can be obtained using the MOI.

FIG. 1A illustrates a surface fatigue crack in an aluminum alloy plate, which is a paramagnetic substance, wherein the surface fatigue crack is detected using an MOI. FIG. 1B illustrates a surface crack in austenite stainless steel formed of a mixture of ferromagnetic and paramagnetic substances, wherein the surface crack is detected using an MOI. In FIG. 1B, the surface crack and a martensite area are illustrated in the austenite stainless steel.

If an object that is to be measured is a paramagnetic substance as shown in FIG. 1A, surface cracks that are indistinguishable to the naked eye can be easily detected from the object using the MOI. However, if an object that is to be measured is a paramagnetic structure locally mixed with a ferromagnetic substance as shown in FIG. 1B, it is very difficult to detect surface cracks in the object using the MOI.

Also, if the MOI is used, it is difficult to quantitatively evaluate the leakage flux generated by the dispersion of an induced current around the surface cracks. In other words, since the MOI provides only image data regarding the surface cracks as shown in FIG. 1A or 1B, it is difficult to quantitatively evaluate actual shapes, sizes, or the like of the surface cracks. In addition, the detected results may be differently interpreted ac cording to the knowledge or skill of an inspector.

DETAILED DESCRIPTION OF THE INVENTION

Technical Problem

The present invention provides a defect detection apparatus for quantitatively analyzing surface defects, near surface defects, and internal surface defects of a ferromagnetic structure, a paramagnetic structure, or a structure formed of a mixture of ferromagnetic and paramagnetic substances, and a magnetic sensor array used in the defect detection apparatus.

Technical Solution

According to an aspect of the present invention, there is provided an apparatus for detecting a defect, including: an induced current applier applying one of line and surf ace currents to an object that is to be measured by using an AC (alternating current) having a frequency varying depending on a depth to be measured; a magneto-electric converter sensing a magnetic field generated from the object by one of the line and surface currents and generating a magnetic field sensing signal corresponding to a strength of the sensed magnetic field; a signal processor filtering and amplifying the magnetic field sensing signal and outputting a signal corresponding to amplitude of the filtered and amplified signal; a signal converter converting the signal output from the signal processor into a digital signal; and a data processor quantitatively converting an intensity of a magnetic field generated from the object into a numerical value based on the digital signal output from the signal converter.

According to another aspect of the present invention, there is provided a magnetic sensor array including: hall sensors arrayed in M rows and N lines; M first power lines; M second power lines; and N first output lines, wherein first power terminals of hall sensors belonging to an $m^{th}$ (where m is a natural number from "1" to "M") row are connected to a first power line in the $m^{th}$ row, second power terminals of the hall sensors belonging to the $m^{th}$ row are connected to a second power line in the $m^{th}$ row, and first output terminals of hall sensors belonging to an $n^{th}$ (where n is a natural number from "1" to "N") line are connected to a first output line in the $n^{th}$ line.

According to another aspect of the present invention, there is provided a magnetic sensor array including: hall sensors arrayed in M rows and N lines, wherein a first power terminal of a hall sensor arrayed in an $m^{th}$ row and an $n^{th}$ line is connected to a second power terminal of a hall sensor arrayed in the $m^{th}$ row and an $n-1^{th}$ line, a second power terminal of the hall sensor arrayed in the $m^{th}$ row and the $n^{th}$ line is connected to a first power terminal of a hall sensor arrayed in the $m^{th}$ row and an $n+1^{th}$ line, a first output terminal of the hall sensor arrayed in the $m^{th}$ row and the $n^{th}$ line is connected to a second output terminal of a hall sensor arrayed in an $m-1^{th}$ row and the $n^{th}$ line, and a second output terminal of the hall sensor arrayed in the $m^{th}$ row and the $n^{th}$ line is connected to a first output terminal of a hall sensor arrayed in an $m+1^{th}$ row and the $n^{th}$ line.

According to another aspect of the present invention, there is provided a magnetic sensor array including: a hall effect material coated on a substrate and having a predetermined size; M first power terminals formed on a first side of the hall effect material; M first power switches respectively connected to the M first power terminals; M second power terminals formed on a second side of the hall effect material; M second power switches respectively connected to the M second power terminals; N first output terminals formed on a third side of the hall effect material; and N second output terminals formed on a fourth side of the hall effect material.

According to another aspect of the present invention, there is provided a magnetic sensor array including: magneto-resistive sensors arrayed in M rows and N lines, wherein a first terminal of a magneto-resistive sensor arrayed in an $m^{th}$ row and an $n^{th}$ line is connected to a second terminal of a magneto-resistive sensor arrayed in the $m^{th}$ row and an $n-1^{th}$ line, a second terminal of the magneto-resistive sensor arrayed in the $m^{th}$ row and the $n^{th}$ line is connected to a first terminal of a magneto-resistive sensor arrayed in the $m^{th}$ row and an $n+1^{th}$ line, a third terminal of the magneto-resistive sensor arrayed in the $m^{th}$ row and the $n^{th}$ line is connected to a fourth terminal of a magneto-resistive sensor arrayed in an $m-1^{th}$ row and the $n^{th}$ line, a fourth terminal of the magneto-resistive sensor arrayed in the $m^{th}$ row and the $n^{th}$ line is connected to a third terminal of a magneto-resistive sensor arrayed in an $m+1^{th}$ row and the $n^{th}$ line, a second terminal of a magneto-resistive sensor arrayed in the $m^{th}$ row and an $N^{th}$ line is connected to a ground voltage through a ground resistor, and a fourth terminal of a magneto-resistive sensor arrayed in an $M^{th}$ row and the $n^{th}$ line is connected to the ground voltage through a ground resistor.

Advantageous Effects

According to the present invention, surface defects, near surface defects, and internal defects of a ferromagnetic structure, a paramagnetic structure, or a structure formed of a mixture of ferromagnetic and paramagnetic substances can be detected. Also, if a defect detection apparatus of the present invention is used, defects such as surface cracks in an object that is to be measured can be quantitatively analyzed.

BEST MODE

A preferred embodiment of the present invention will now be described with reference to the attached drawings.

Figure 2:
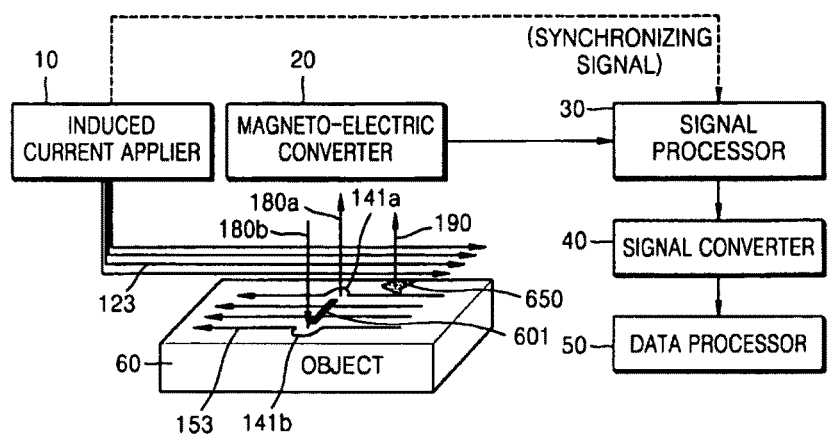
FIG. 2 illustrates an apparatus for detecting defects of a ferromagnetic structure, a paramagnetic structure, or a structure formed of a mixture of ferromagnetic and paramagnetic substances, according to an embodiment of the present invention.

FIG. 2 illustrates an apparatus for detecting defects of a ferromagnetic structure, a paramagnetic structure, or a structure formed of a mixture of ferromagnetic and paramagnetic substances, according to an embodiment of the present invention. An object 60 that is to be measured, an induced current applier 10, a magneto-electric converter 20, a signal processor 30, a signal converter 40, and a data processor 50 are shown in FIG. 2.

If the induced current applier 10 applies a line or surface current 123 to the object 60, an induced line or surface current 153 is induced in the object 60. If the induced line or surface current 153 is dispersed around a surface crack 601 as shown in FIG. 2, i.e., paths of the induced line or surface current 153 is changed like 141a and 141b, m agnetic fields 180a and 180b are generated around the surface crack 601 perpendicular to a surface of the object 60. If the object 60, which is a paramagnetic substance, is locally mixed with a ferromagnetic substance 650, a magnetic field 190 is generated by residual magnetization of the ferromagnetic substance 650. The magnetic fields 180a and 180b, formed by the surface crack 601, may be hereinafter called alternating current (AC) magnetic fields 180a and 180b, and the magnetic field 190 formed by the ferromagnetic substance 650 may be hereinafter called a direct current (DC) magnetic field 190. In the present invention, the signal processor 30 can separate the components of the AC magnetic fields 180a and 180b from a component of the DC magnetic field 190, as described later with reference to FIG. 5.

Figure 3A:
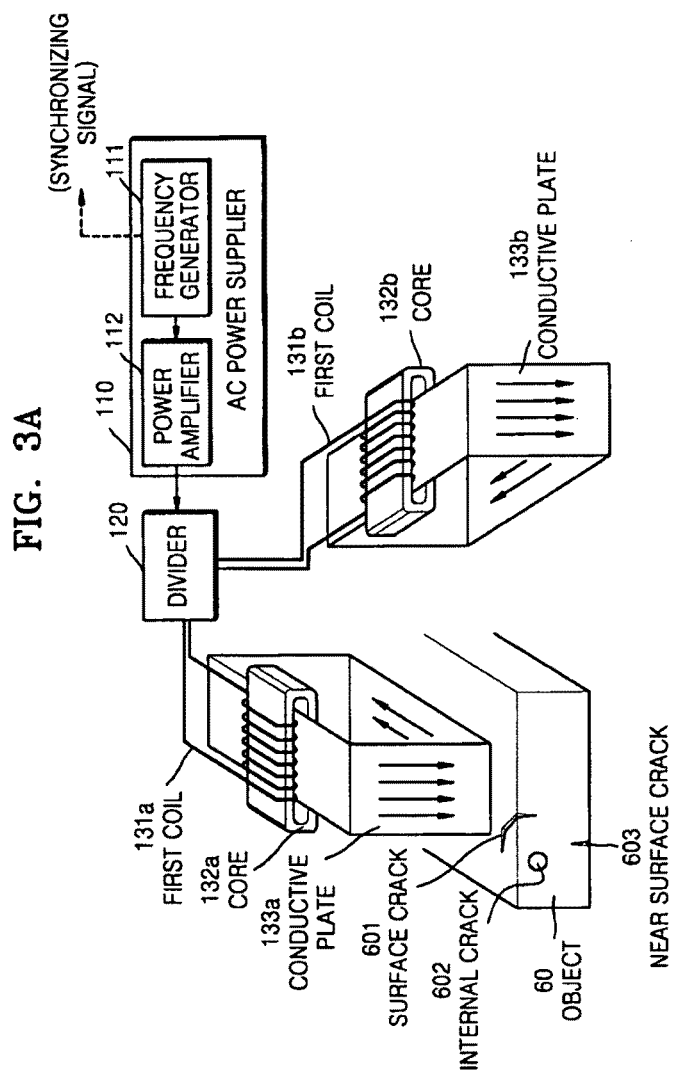
FIG. 3A illustrates an inducted current applier illustrated in FIG. 2 in detail.

FIG. 3A illustrates the inducted current applier 10 illustrated in FIG. 2 in detail. Referring to FIG. 3A, the induced current applier 10 includes an AC power source supplier 110, a divider 120, one or more first coils 131a and 131b, one or more cores 132a and 132b, and one or more conductive plates 133a and 133b. The cores 132a and 132b may be cores formed of a ferromagnetic material including ferrite and permalloy, and the conductive plates 133a and 133b may be conductive plates formed of a copper, gold silver, or aluminum material. As shown in FIG. 3A, the conductive plate 133a may be disposed so that a portion thereof is adhered to the object 60.

The AC power source supplier 110 generates an AC that is supplied to the first coils 131a and 131b through the divider 120. The cores 132a and 132b mediate induction operations between the first coils 131a and 131b and the conductive plates 133a and 133b. If the widths of the conductive plates 133a and 133b are fully less than the lengths of the conductive plates 133a and 133b, the AC may be directly applied to the conductive plates 133a and 133b without using the cores 132a and 132b. The conductive plates 133a and 133b apply the line or surface current 123, as shown in FIG. 2, induced by the AC to the object 60. If the line or surface current 123 is applied to the object 60, a magnetic field is generated by leakage flux around the surface crack 601, a near surface crack 603, or an internal crack 602 of the object 60.

As shown in FIG. 3A, the AC power source supplier 110 includes a frequency generator 111 and a power amplifier 112. The frequency generator 111 generates the AC having a predetermined frequency, and the frequency generator 111 can also output a synchronizing signal to the signal processor 30 to control an operation of the signal processor 30 as described later in detail with reference to FIG. 5. The power amplifier 112 amplifies the power of the AC generated by the frequency generator 111, and the AC power source supplier 110 may supply ACs having various waveforms such as a sine wave, a half-rectifying wave, a pulse wave, etc. The AC power source supplier 110 can also vary the frequency of the AC depending on the depth to be measured from the surface of the object 60. For example, if the surface crack 601 is to be detected, the AC power source supplier 110 may use a low or high frequency. If the near surface crack 603 or the internal crack 602 is to be detected, the AC power source supplier 110 may use a low frequency based on the physical principle that a low frequency signal can deeply infiltrate the object 60.

If the induced current applier 10 only includes one first coil, one core, and one conductive plate, the divider 120 is not needed. However, a plurality of first coils, cores, and conductive coils can be used, and thus, as shown in the present embodiment, the first coils 131a and 131b, the cores 132a and 132b, and the conductive plates 133a and 133b may be used to detect cracks of the object 60 from various angles. In this case, the divider 120 divides the AC output from the AC power source supplier 110 so as to distribute the AC to the first coils 131a and 131b, respectively. The divider 120 control the phases of the ACs that are respectively distributed to the first coils 131a and 131b. In detail, the divider 120 controls the phases of the ACs that are respectively distributed to the first coils 131a and 131b in consideration of an angle between the conductive plates 133a and 133b. As a result, a predetermined difference exists between the phases of a line or surface current induced on one of the conductive plates 133a and 133b and a line or surface current inducted on the other one of the conductive plates 133a and 133b.

Figure 3B:
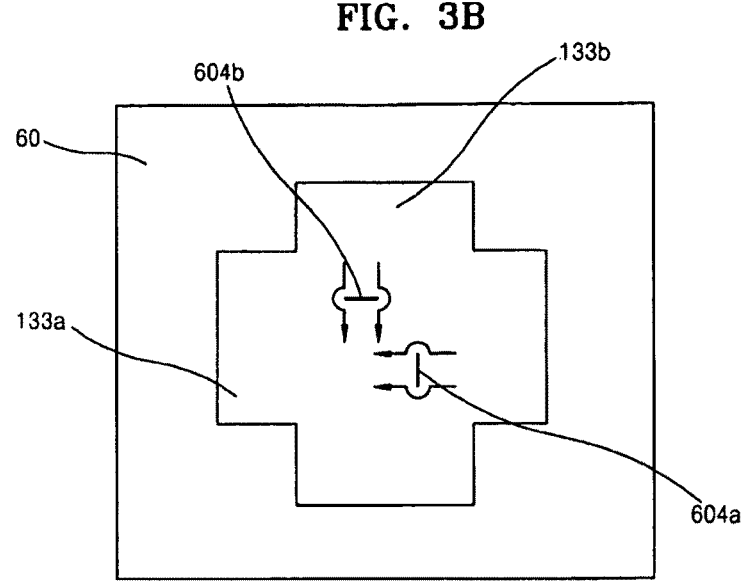
FIG. 3B illustrates arrangements of conductive plates.

FIG. 3B illustrates arrangements of the conductive plates 133a and 133b. Referring to FIG. 3B, portions of the conductive plates 133a and 133b are adhered to the object 60. An inducted current is dispersed around cracks 604a and 604b of the object 60. As shown in FIG. 3B, the conductive plates 133a and 133b may be arranged so as to form a right angle therebetween. If the directions of the induced currents are equal to the longitudinal directions of the cracks 604a and 604b of the object 60 in the conductive plates 133a and 133b or the angles between the directions of the induced currents and the longitudinal directions of the cracks 604a and 604b are small, the dispersion of the induced currents is reduced around the cracks 604a and 604b. Thus, the generation of a magnetic field by leakage flux is reduced. In such case, it is difficult to detect the cracks 604a and 604b of the object 60. In the present invention, the conductive plates 133a and 133b are arranged to form a right angle with each other so that the induced current is largely dispersed around the cracks 604a and 604b. If the conductive plates 133a and 133b are arranged at right angle to each other, the cracks 604a and 604b can be detected regardless of the longitudinal directions of the cracks 604a and 604b.

However, even if only the conductive plate 133a is included, the conductive plate 133a may be rotated in various directions on the surface of the object 60 to detect the cracks 604a and 604b regardless of the longitudinal directions of the cracks 604a and 604b. Also, if only the conductive plate 133a is included, as previously described, the divider 120 is not needed.

Figure 3C:
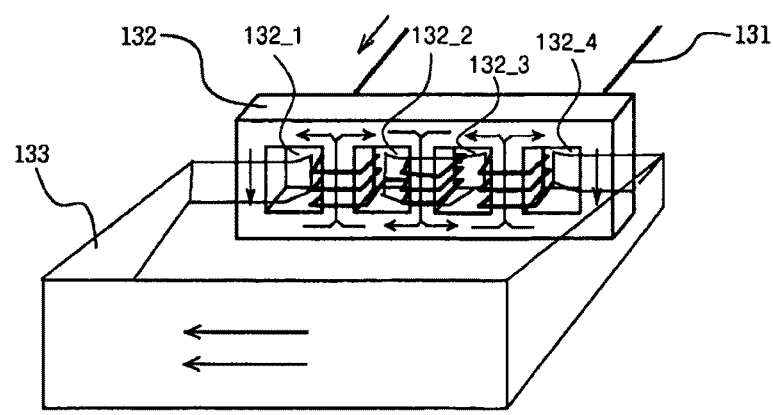
FIG. 3C illustrates a combined structure of a first coil, a core, and a conductive plate.

FIG. 3C illustrates a combined structure of a first coil 131, a core 132, and a conductive plate 133. Referring to FIG. 3C, the core 132 includes a plurality of through paths 132_1, 132_2, 132_3, and 132_4. If the conductive plate 133 passes the through paths 132_1, 132_2, 132_3, and 132_4, a line or surface current applied to the object 60 may be strengthened. In other words, an area of the conductive plate 133 penetrating the core 132 may be increased to strengthen a line or surface current induced on the conductive plate 133. If the line or surface current induced on the conductive plate 133 is strengthened, the line or surface current applied to the object 60 is also strengthened. In this case, the strength of a magnetic field by leakage flux generated around a crack of the object 60 is strengthened, and thus, the crack of the object 60 can be easily detected. In other words, the strength of the magnetic field by the leakage flux generated around the crack of the object 60 can be strengthened, thereby improving a detection capability.

The magneto-electric converter 20 of FIG. 2 senses the AC magnetic fields 180a and 180b, and the DC magnetic field 190 that are generated from the object 60 due to the line or surface current 153, and the magneto-electric converter 20 generates magnetic field sensing signals corresponding to the strengths of the AC magnetic fields 180a and 180b, and the DC magnetic field 190. The magneto-electric converter 20 may be realized using a hall sensor, a hall integrated circuit (IC), a magneto-resistive sensor, or a giant magneto-resistive sensor. The magneto-electric converter 20 will now be described in detail with reference to FIGS. 4A through 4J.

Figure 4A:
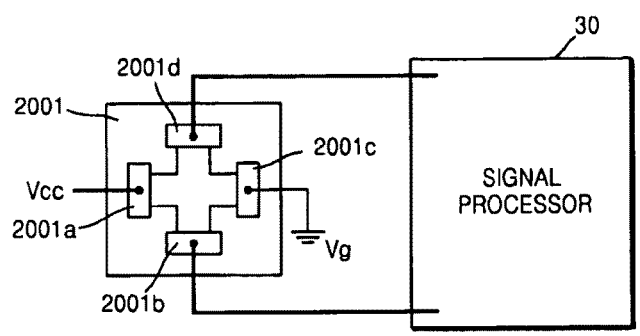
FIG. 4A illustrates a hall sensor and a signal processor.
Figure 4B:
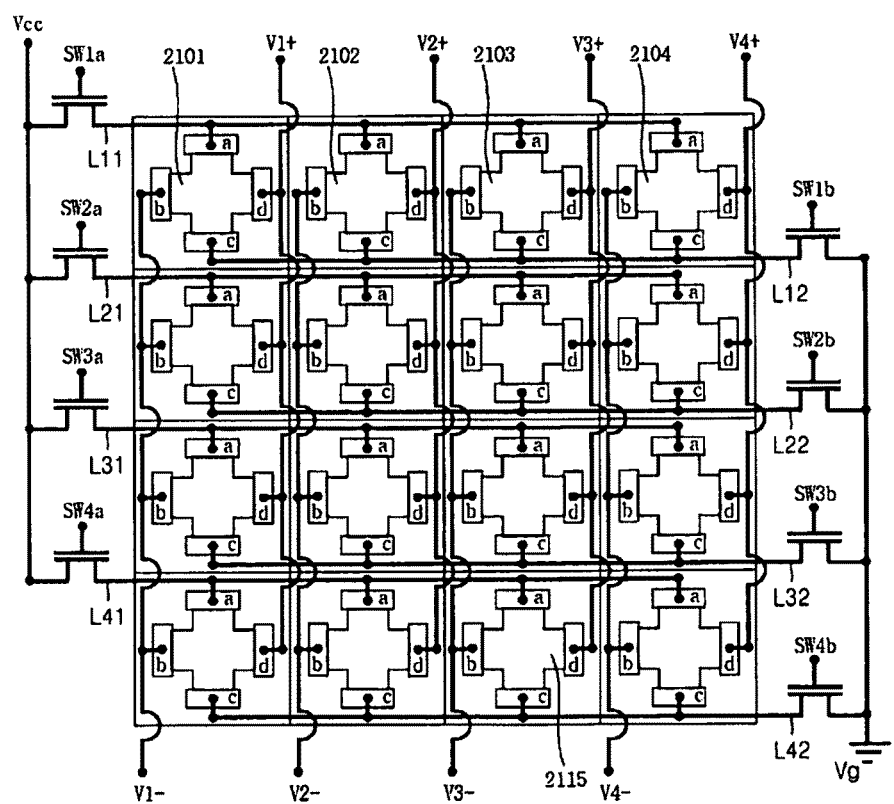
FIGS. 4B through 4I illustrate hall sensor arrays according to embodiments of the present invention.
Figure 4C:
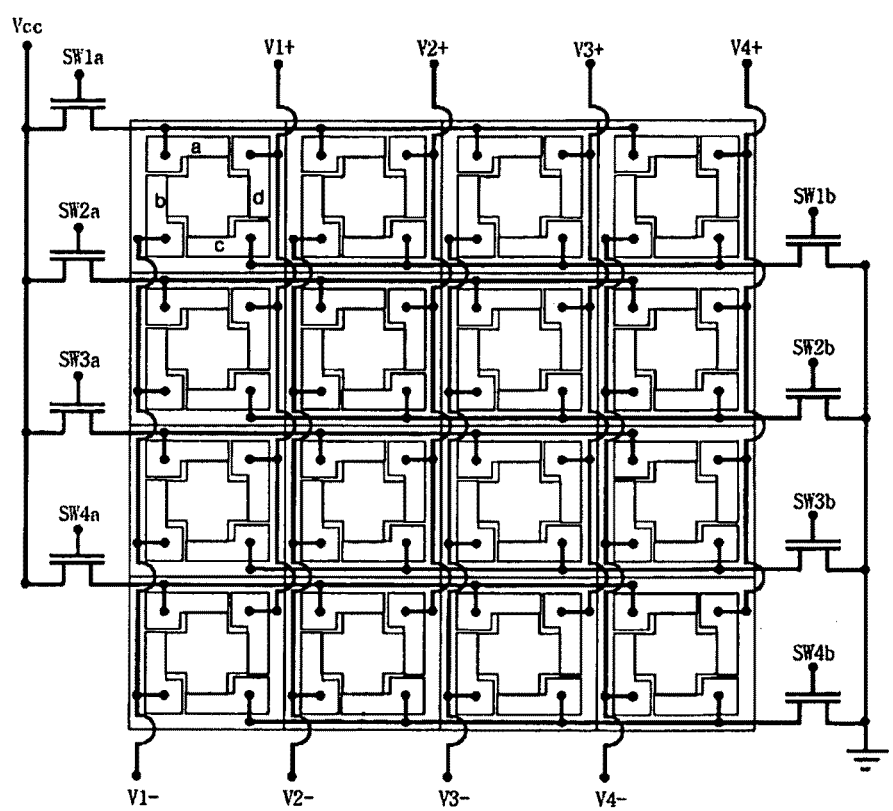
Figure 4D:
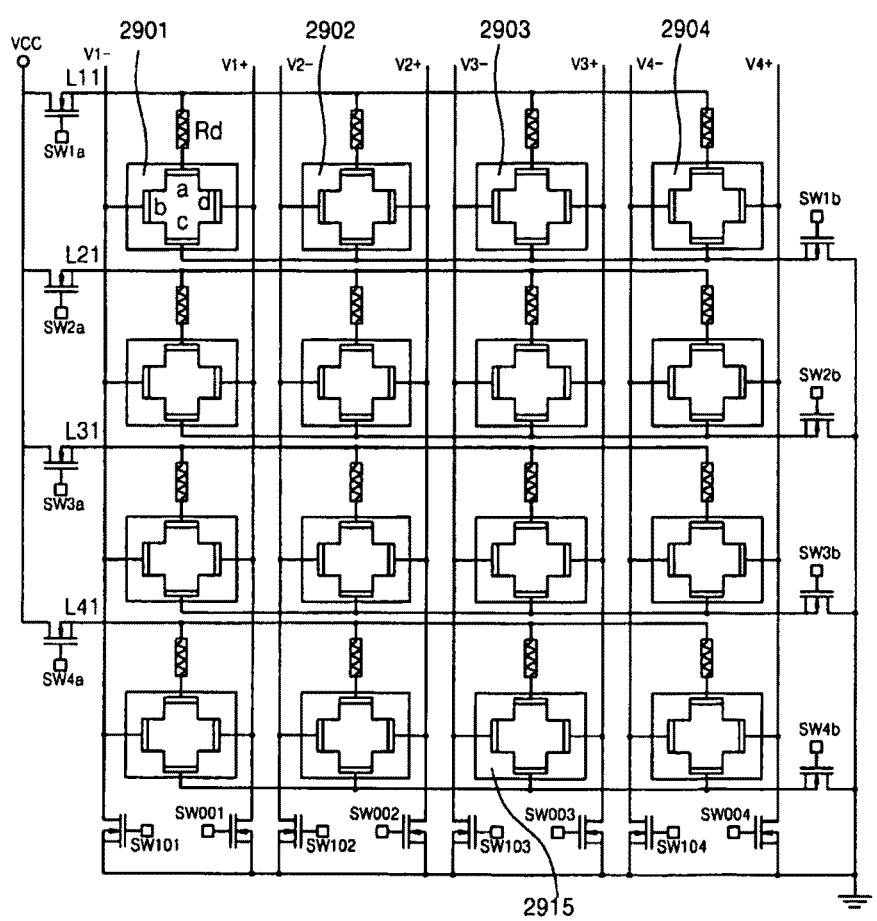
Figure 4E:
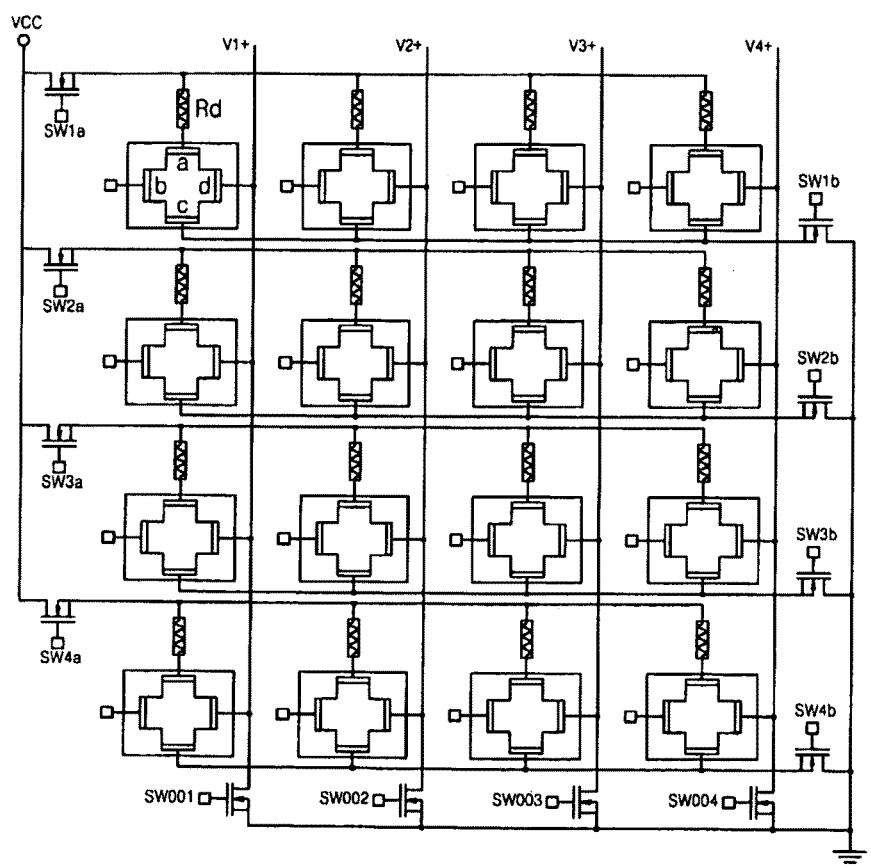
Figure 4F:
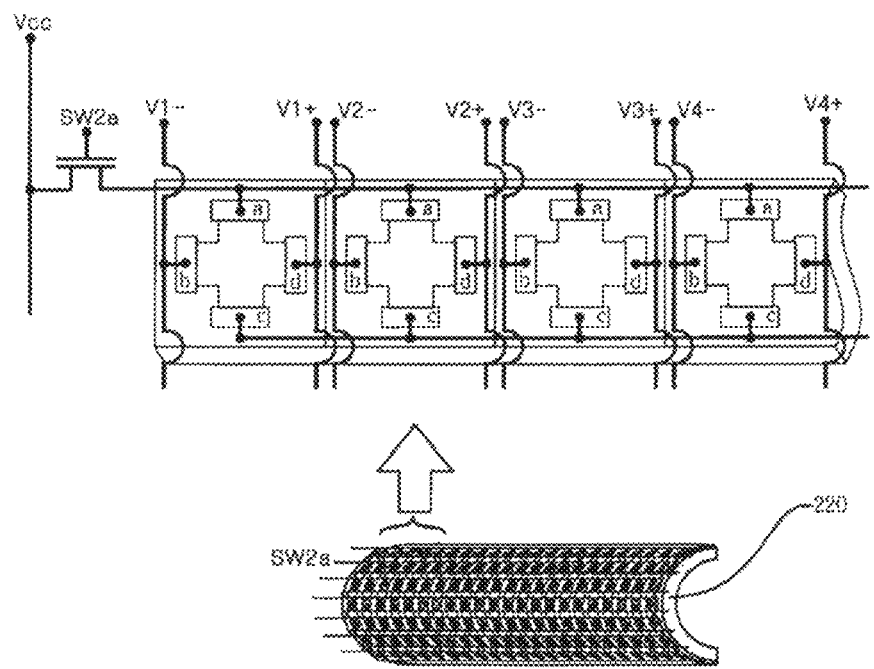
Figure 4G:
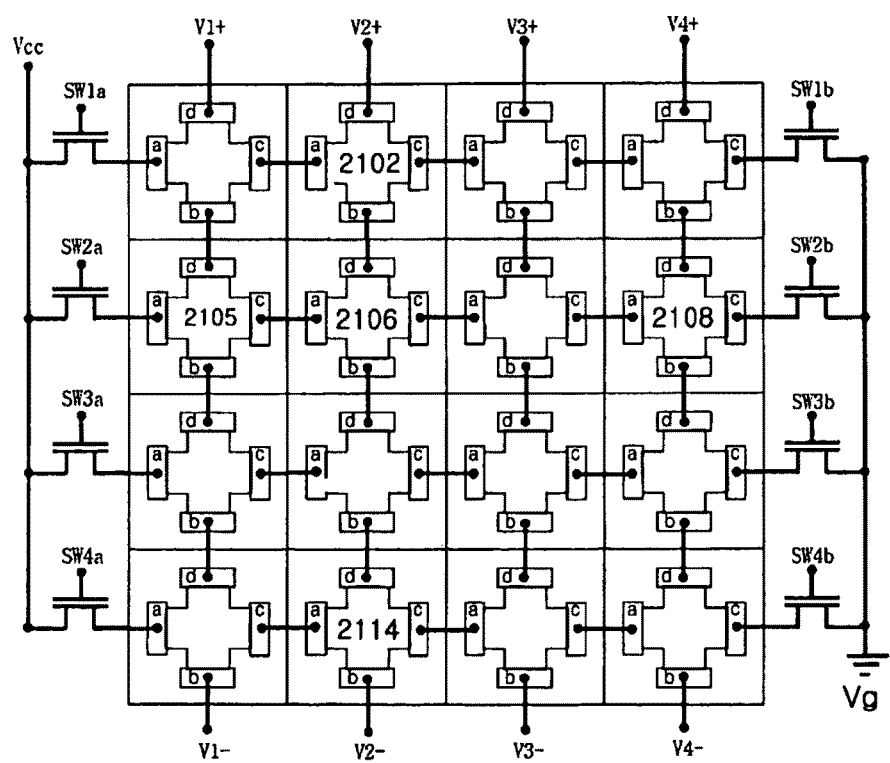
Figure 4H:
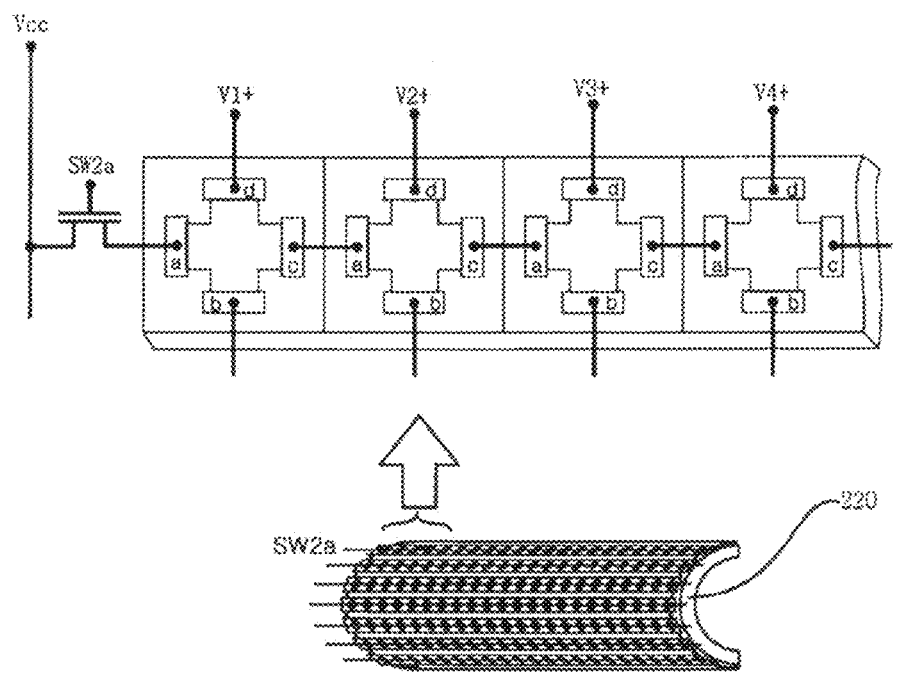
Figure 4I:
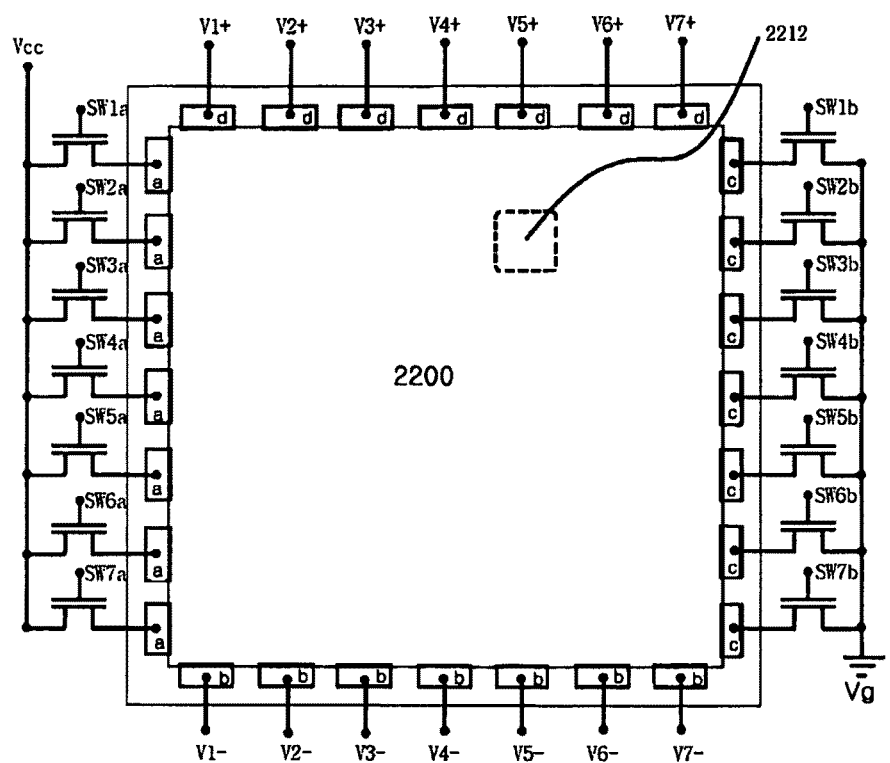
Figure 4J:
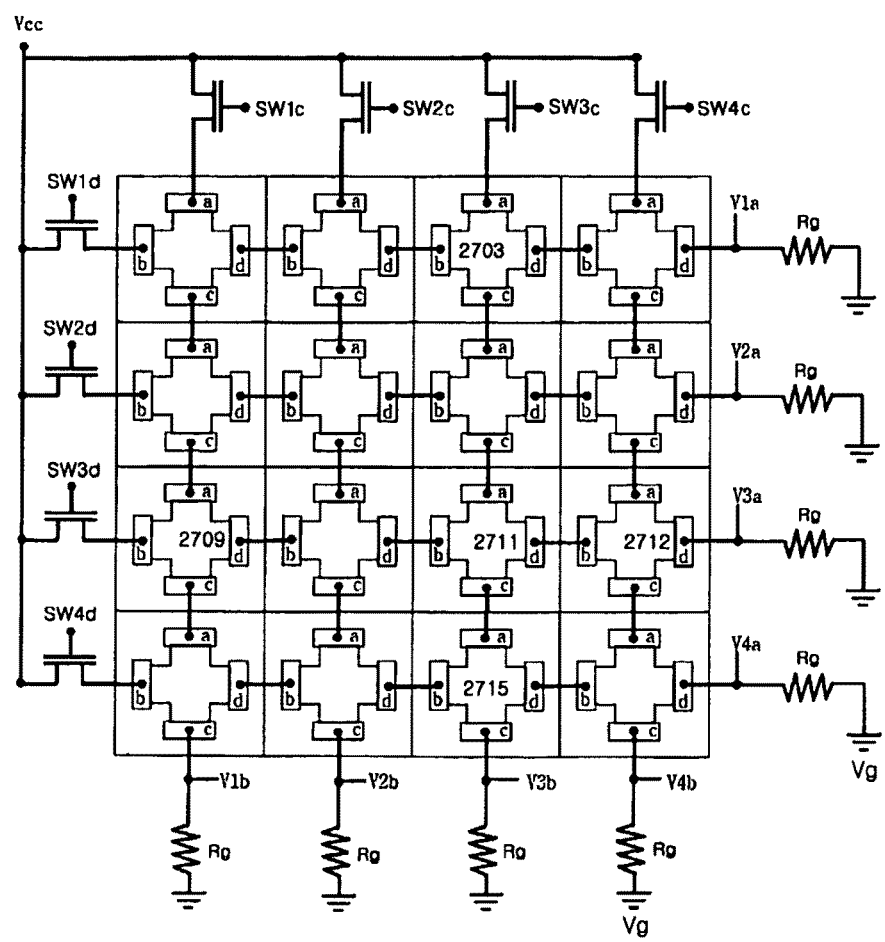
FIG. 4J illustrates a magneto-resistive sensor array according to an embodiment of the present invention.

FIG. 4A illustrates a hall sensor and a signal processor, FIGS. 4B through 4I illustrates hall sensor arrays according to embodiments of the present invention, and FIG. 4J illustrates a magneto-resistive sensor array according to an embodiment of the present invention.

The magneto-electric converter 20 of FIG. 2 may include a hall sensor 2001 shown in FIG. 4A, the hall sensor array shown in FIGS. 4B through 4I, or the magneto-resistive sensor array shown in FIG. 4J.

As shown in FIG. 4A, the hall sensor 2001 includes first and second power terminals 2001a and 2001c and first and second output terminals 2001d and 2001b. If a first power source voltage Vcc is applied to the first power terminal 2001a, and a second power source voltage Vg is applied to the second power terminal 2001c, the hall sensor 2001 outputs magnetic field sensing signal, corresponding to the strength of the magnetic field incident onto the hall sensor 2001, to the signal processor 30 through the first and second output terminals 2001d and 2001b. If an electric field and a magnetic field are orthogonal to each other in the hall sensor 2001, a voltage difference occurs between the first and second output terminals 2001d and 2001b, and a magnetic field sensing signal is generated corresponding to the voltage difference between the first and second output terminals 2001d and 2001b. The magneto-electric converter 20 may include a hall IC, which is a device onto which a hall sensor and a differential amplifying circuit are integrated.

A single hall sensor can be precisely moved on a plane parallel with the object 60 to sense a magnetic field generated around a crack of the object 60. In this method, the single hall sensor must be moved so as to precisely scan the object 60. The magnetic field generated around the crack of the object 60 may be sensed using a 1-dimensional magnetic sensor array, a 2-dimensional magnetic sensor array, or a 3-dimensional magnetic sensor array besides a single magnetic sensor.

The hall sensor array shown in FIG. 4B includes hall sensors, for example, 2101, 2102, 2103, 2104, and 2115, which are arrayed in M rows and N lines (4 rows and 4 lines are shown in FIG. 4B, however the present invention is not limited thereto). That is, the hall sensor array includes M first power lines L11, L21, L31, through LM1, M second power lines L12, L22, L32, through LM2, N first output lines V1+, V2+, V3+, through VN+, and N second output lines V1−, V2−, V3−, through VN−, where N and M are a natural number. In the present embodiment, for convenience of explanation, 4 first power lines L11, L21, L31, and L41, 4 second power lines L12, L22, L32, and L42, 4 first output lines V1+, V2+, V3+, and V4+, and 4 second output lines V1−, V2−, V3−, and V4− are illustrated. As shown in FIG. 4B, first power terminals a of hall sensors belonging to the m$^{th}$ (where m is a natural number from "1" to "M.") row are connected to a first power line Lm1 of the $m^{th}$ row, and second power terminals c of the hall sensors belonging to the $m^{th}$ row are connected to a second power line Lm2 of the $m^{th}$ row. First output terminals d of hall sensors belonging to the $n^{th}$ (where n is a natural number from "1" to "N.") line are connected to a first output line Vn+ of the $n^{th}$ line, and second output terminals b of the hall sensors belonging to the $n^{th}$ line are connected to a second output line Vn− of the $n^{th}$ line. A switch SW1a transmits a first power source voltage Vcc to the first power line L11 of the first row, and a switch SW1b transmits a second power source voltage Vg to the second power line L12 of the first row. Similarly, a switch SW4a transmits the first power source voltage Vcc to the first power line L41 of the fourth row, and a switch SW4b transmits the second power source voltage Vg to the second power line L42 of the fourth row.

If the first power source voltage Vcc is applied to the first power line Lm1 of the $m^{th}$ row, and the second power source voltage Vg is applied to the second power line Lm2 of the $m^{th}$ row, the hall sensor arrayed in the $m^{th}$ row and the $n^{th}$ line outputs a magnetic field sensing signal corresponding to the strength of a magnetic field, which is gene rated from the object 60 and incident onto the hall sensor, through the first and second output lines Vn+ and Vn− of the $n^{th}$ line. For example, if the switches SW1a and SW1b are turned on, the hall sensor 2102 arrayed in the first row and the second line outputs a magnetic field sensing signal corresponding to the strength of a magnetic field incident onto the hall sensor 2102 through first and second output lines V2+ and V2− of the second line. If the switches SW4a and SW4b are turned on, the hall sensor 2115 arrayed in the fourth row and the third line outputs a magnetic field sensing signal corresponding to the strength of a magnetic field incident onto the hall sensor 2115 through first and second output lines V3+ and V3− of the third line.

The hall sensor array shown in FIG. 4C is very similar to the hall sensor array shown in FIG. 4B. However, the pad shapes of terminals a, b, c, and d of the hall sensor are slightly different.

The hall sensor array shown in FIG. 4D further includes resistors Rd that are arrayed in M rows and N lines. As shown in FIG. 4D, a first power terminal a of a hall sensor arrayed in an $m^{th}$ row and an $n^{th}$ line is connected to a first power line Lm1 of the $m^{th}$ row through the resistor Rd arrayed in the $m^{th}$ row and the $n^{th}$ line. The operation conditions of hall sensors arrayed in M rows and N lines can be adjusted to be the same us ing the resistors Rd arrayed in the M row and the N lines.

The hall sensor array of FIG. 4D further includes switches SW001, SW002, SW003, and SW004 that respectively control first output lines V1+, V2+, V3+, and V4+, and switches SW101, SW102, SW103, and SW104 that respectively control second output lines V1−, V2−, V3−, and V4−. For example, in the present embodiment, if switches SW1a and SW1b are turned on, switches SW2a, SW2b, SW3a, SW3b, SW4a, and SW4b are turned off, and the switches SW001, SW101, SW002, SW102, SW003, SW103, SW004, and SW104 are turned off, the strengths of magnetic fields respectively incident onto hall sensors 2901, 2902, 2903, and 2904 belonging to the first row can be sense d. If the switches SW1a, SW1b, SW2a, SW2b, SW3a, and SW3b are turned off, the switches SW4a and SW4b are turned on, the switches SW001, SW101, SW002, SW102, SW004, SW104 are turned on, and the switches SW003 and SW103 are turned off, the strength of a magnetic field incident onto a hall sensor 2915 belonging to the fourth row and the third line can be sensed. The strength of a magnetic field may be sensed in the row unit or cell unit as described above.

Different from the hall sensor array illustrated in FIG. 4B or 4D, the hall sensor array illustrated in FIG. 4E does not include N second output lines V1−, V2−, V3−, and V4−. When a hall sensor arrayed in an $m^{th}$ row and an $n^{th}$ line in the hall sensor array of FIG. 4E outputs a magnetic field sensing signal through a first output line Vn+ of the $n^{th}$ line, a second output terminal b of the hall sensor is in floating state. According such result, even when the second output terminal b of the hall sensor arrayed in the $m^{th}$ row and the $n^{th}$ line is in the floating state or is grounded, the hall sensor can normally output the magnetic field sensing signal through the first output line Vn+ of the $n^{th}$ line. However, in this case, a signal processing process of the signal processor 30 becomes more complicated.

A hall sensor array as described above may be arrayed on a 2-dimensional plane, however may also be arrayed on a 3-dimensional cylindrical curved surface 220 as shown in FIG. 4F. If the hall sensor array is arrayed on the 3-dimensional cylindrical curved surface 220 and the object 60 is a cylindrical pipe, cracks in an interior or exterior of the cylindrical pipe can be easily detected.

In the hall sensor array shown in FIG. 4G, terminals of hall sensors arrayed in M rows and N lines are connected to one another in series. In other words, a first power terminal a of a hall sensor arrayed in an $m^{th}$ row and an $n^{th}$ line is connected to a second power terminal c of a hall sensor arrayed in the $m^{th}$ tow and an $n-1^{th}$ line. A second power terminal c of the hall sensor arrayed in the $m^{th}$ row and the $n^{th}$ line is connected to a first power terminal a of a hall sensor arrayed in the $m^{th}$ row and an $n+1^{th}$ line. A first output terminal d of the hall sensor arrayed in the $m^{th}$ row and the $n^{th}$ line is connected to a second output terminal b of a hall sensor arrayed in an $m-1^{th}$ row and the $n^{th}$ line. A second output terminal b arrayed in the $m^{th}$ row and an $n^{th}$ line is connected to a first output terminal d of a hall sensor arrayed in an $m+1^{th}$ row and the $n^{th}$ line.

If a first power source voltage Vcc is applied to a first power terminal a of a hall sensor 2105 arrayed in the second row and the first line, and a second power source voltage Vg is applied to a second power terminal c of a hall sensor 2108 arrayed in the second row and the fourth line as shown in FIG. 4G, a voltage difference between a first output terminal d of a hall sensor 2102 arrayed in the first row and the second line and a second output terminal b of a hall sensor 2114 arrayed in the fourth row and the second line is output as a magnetic field sensing signal corresponding to the strength of a magnetic field that is generated from the object 60 and incident onto a hall sensor 2106 arrayed in the second row and the second line.

The hall sensor array of FIG. 4G may be arrayed on the 3-dimensional cylindric al curved surface 220 as shown in FIG. 4H.

The hall sensor array shown in FIG. 4I includes a hall effect material 2200, M first power terminals a, M first power switches SW1a through SW7a, M second power terminals c, M second power switches SW1b through SW7b, N first output terminals d, and N second output terminals b. The hall effect material 2200 has a predetermined size and is coated on a substrate. The M first power terminals a are formed on a first side of the hall effect material 2200. The M first power switches SW1a through SW7a are respectively connected to the M first power terminals a. The M second power terminals c are formed on a second side of the hall effect material 2200. The M second power switches SW1b through SW7b are respectively connected to the M second power terminals c. The N first output terminals d are formed on a third side of the hall effect material 2200. The N second output terminals b are formed on a fourth side of the hall effect material 2200.

The hall effect material 2200 of FIG. 4I may be divided into M rows and N lines (7 rows and 7 lines as shown in FIG. 4I). If first and second power switches SWma and SWmb in an $m^{th}$ row are turned on, a voltage difference between first and second output terminals d and b in an $n^{th}$ line is output as a magnetic field sensing signal corresponding to the strength of a magnetic field that is generated from the object 60 and incident onto a portion of the hall effect material 2200 in the $m^{th}$ row and the $n^{th}$ line. For example, if first and second power switches SW2a and SW2b in the second row are turned on, a voltage difference (i.e., a difference between voltages V5+ and V5−) between first and second output terminals d and b in the fifth line is output as a magnetic field sensing signal corresponding to the strength of a magnetic field that is generated from the object 60 and incident onto a portion 2212 of the hall effect material 2200 in the second row and the fifth line.

The magneto-resistive sensor array of FIG. 4J includes magneto-resistive sensors that are arrayed in M rows and N lines, switches SW1c through SW4c and SW1d through SW4d that transmit a power supply voltage Vcc, and ground resistors Rg that are connected to a ground voltage Vg.

In the magneto-resistive sensor array of FIG. 4J, a first terminal b of a magneto-resistive sensor arrayed in an $m^{th}$ row and an $n^{th}$ line is connected to a second terminal d of a magneto-resistive sensor arrayed in the $m^{th}$ row and an $n-1^{th}$ line. A second terminal d of the magneto-resistive sensor arrayed in the $m^{th}$ row and the $n^{th}$ line is connected to a first terminal b of a magneto-resistive sensor arrayed in the $m^{th}$ row and an $n+1^{th}$ line. A third terminal a of the magneto-resistive sensor arrayed in the $m^{th}$ row and the $n^{th}$ line is connected to a fourth terminal c of a magneto-resistive sensor arrayed in an $m-1^{th}$ row and the $n^{th}$ line. A fourth terminal c of the magneto-resistive sensor arrayed in the $m^{th}$ row and the $n^{th}$ line is connected to a third terminal a of a magneto-resistive sensor arrayed in an $m+1^{th}$ row and the $n^{th}$ line. A second terminal d of a magneto-resistive sensor arrayed in the $m^{th}$ row and an $N^{th}$ line is connected to the ground voltage Vg through a ground resistor Rg. A fourth terminal c of a magneto-resistive sensor arrayed in the $M^{th}$ row and the $n^{th}$ line is connected to the ground voltage Vg through a ground resistor Rg.

For example, in order to sense the strength of a magnetic field that is generated from the object 60 and incident onto a magneto-resistive sensor 2711 arrayed in the third row and the third line, the power supply voltage Vcc is applied to a first terminal b of a magneto-resistive sensor 2709 arrayed in the third row and the first line to measure a voltage V3a of a second terminal d of a magneto-resistive sensor 2712 arrayed in the third row and the fourth line. Also, the power supply voltage Vcc is applied to a third terminal a of a magneto-resistive sensor 2703 arrayed in the first row and the third line to measure a voltage V3b of a fourth terminal c of a magneto-resistive sensor 2715 arrayed in the fourth row and the third line. The strength of the magnetic field incident onto the magneto-resistive sensor 2711 can be calculated based on the measured voltages V3a and V3b.

Figure 5:
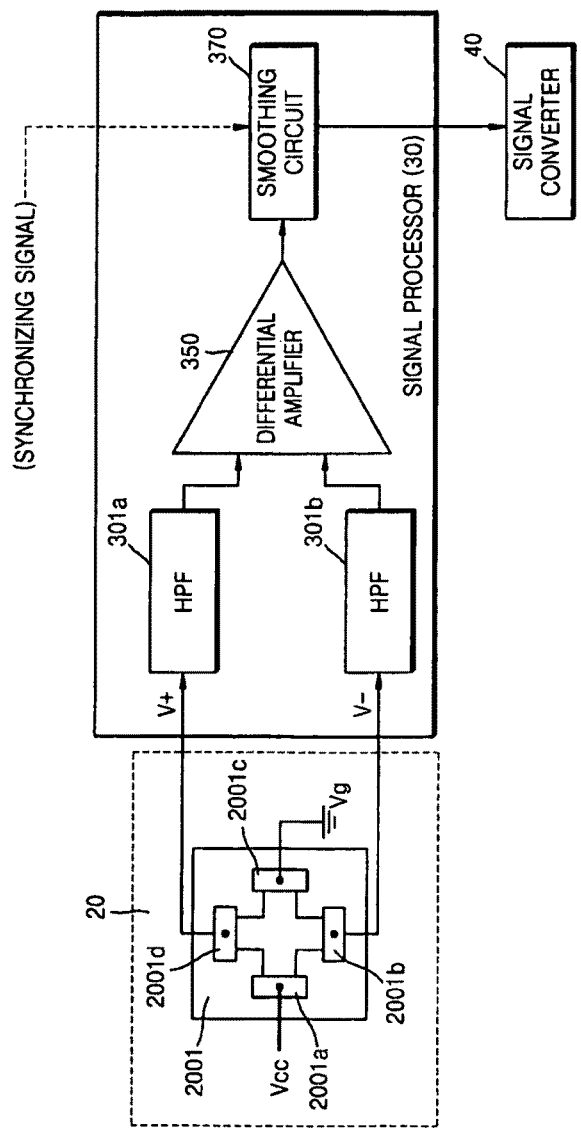
FIG. 5 is a detailed block diagram of a signal processor illustrated in FIG. 2, according to an embodiment of the present invention.

FIG. 5 is a block diagram of the signal processor 30 of FIG. 2. The magneto-electric converter 20, the signal processor 30, and the signal converter 40 are shown in FIG. 5.

The signal processor 30 filters and amplifies magnetic field sensing signals V+ and V− output from the magneto-electric converter 20 and outputs a signal corresponding to the amplitude of the filtered and amplified signal. The signal processor 30 of FIG. 5 includes high pass filters (HPFs) 301a and 301b, a differential amplifier 350, and a smoothing circuit 370. The HPFs 301a and 301b and the differential amplifier 350 may be disposed in a reverse order in the signal processor 30 of FIG. 5.

If the line or surface current 123 is applied to the object 60, as described with reference to FIG. 2, the AC magnetic fields 180a and 180b and the DC magnetic field 190 are simultaneously generated due to the surface crack 601 and the ferromagnetic substance 650, respectively. The magnetic field sensing signals V+ and V− output from the magneto-electric converter 20 include the components of the AC magnetic fields 180a and 180b and the DC magnetic field 190. The HPFs 301a and 301b remove the component of the DC magnetic field 190 from the magnetic field sensing signals V+ and V−. The magnetic field sensing signals V+ and V−, from which the component of the DC magnetic field 190 has been removed, are differentially amplified by the differential amplifier 350. The smoothing circuit 370 outputs a signal corresponding to the amplitude of the differentially amplified signal. A root mean square circuit, a lock-in-amplifier, or a maximum value detecting circuit may be used as the smoothing circuit 370, so as to output the signal corresponding to the amplitude of the differentially amplified signal. In particular, if the lock-in-amplifier is used as the smoothing circuit 370, the lock-in-amplifier may receive the synchronizing signal output from the frequency generator 111 shown in FIG. 3A.

In the present invention, the signal processor 30 may remove the components of the AC magnetic fields 180a and 180b and output an amplitude signal corresponding the DC magnetic field 190 in order to detect the ferromagnetic substance locally mixed with the object 60, which is the paramagnetic substance. In this case, low pass filter (LPFs) may be used instead of the HPFs 301a and 301b. If the filters of the signal processor 30 are appropriately selected as described above, the cracks 601, 602, and 603 of the object 60 may be detected, and the ferromagnetic substance mixed with the object 60, which is the paramagnetic substance, may be detected. HPFs, LPFs, or band pass filters (BPFs) may be appropriately selected to selectively extract the component of the AC magnetic fields 180a and 180b or the component of the DC magnetic field 190.

The signal converter 40 of FIG. 2 converts a signal output from the signal processor 30 into a digital signal. The signal converter 40 may include analog-to-digital converters (ADCs), wherein the number of ADCs may be equal to or less than the number of magnetic sensors of the magneto-electric converter 20. If the number of ADCs of the signal converter 40 is less than the number of magnetic sensors of the magneto-electric converter 20, multiplexers may be used instead.

The data processor 50 of FIG. 2 quantitatively converts the strength of a magnetic field generated from the object 60 into a numerical value based on a signal output from the signal converter 40. For example, the data processor 50 calculates the amplitude of a magnetic field generated from each position of the object 60, a differential value (dB/dx) of the amplitude with respect to a horizontal direction of the surface current, a differential value (dB/dy) of the amplitude with respect to a vertical direction of the surface current, and a differential value (dB^2/dxdy) of the amplitude with respect to horizontal and vertical directions of the surface current, and converts the differential values into numerical values. Thus, cracks of the object 60 can be quantitatively analyzed with such numerical values. In other words, positions, directions, shapes, and sizes of the cracks of the object 60 can be quantitatively analyzed.

Figure 1A:
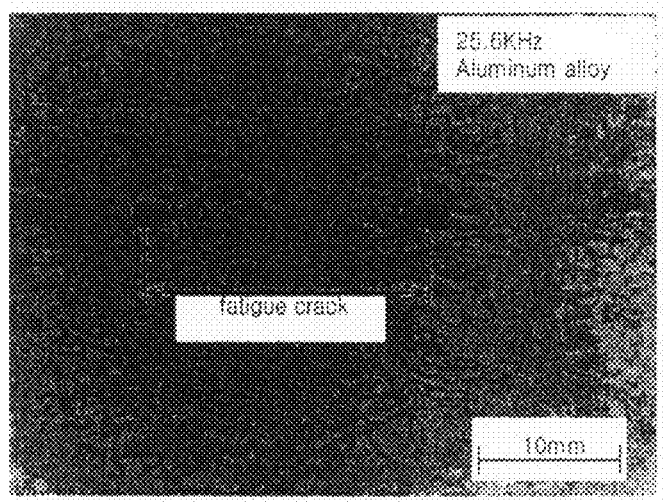
FIG. 1A illustrates a surface fatigue crack in an aluminum alloy plate, which is a paramagnetic substance, wherein the surface fatigue crack is detected using a Magneto-Optical eddy current Imager (MOI).
Figure 1B:
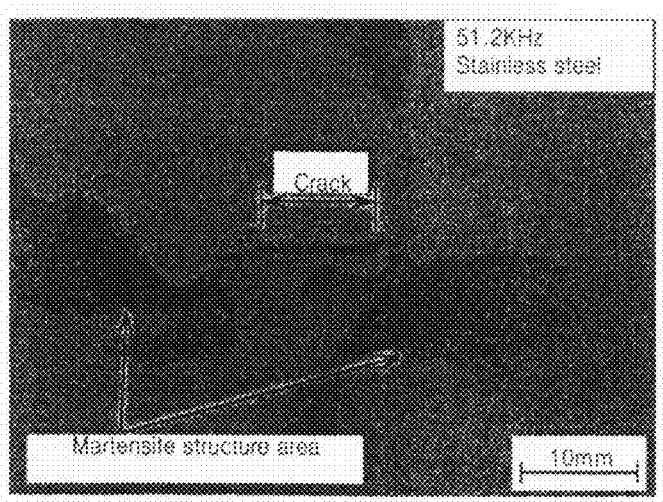
FIG. 1B illustrates a surface crack in austenite stainless steel formed of a mixture of ferromagnetic and paramagnetic substances, wherein the surface crack is detected using an MOI.

FIGS. 6A through 6D illustrate surface cracks of an object formed of a mixture of ferromagnetic and paramagnetic substances, which are detected by using a defect detection apparatus of the present invention. The object measured and illustrated in FIGS. 6A through 6D is the same as an object that is to be measured as shown in FIG. 1B.

Figure 6A:
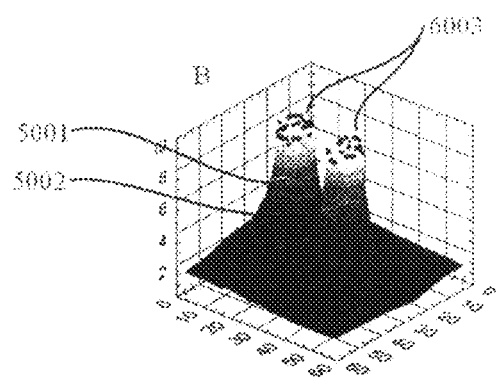
FIGS. 6A through 6D illustrate surface cracks of an object formed of a mixture of ferromagnetic and paramagnetic substances, which are detected by using a defect detection apparatus of the present invention.
Figure 6B:
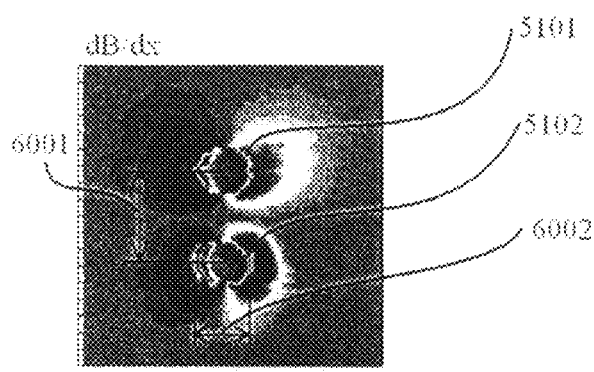
Figure 6C:
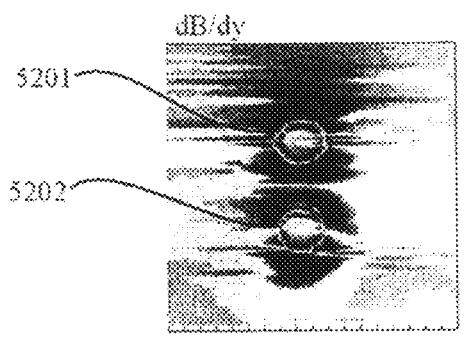
Figure 6D:
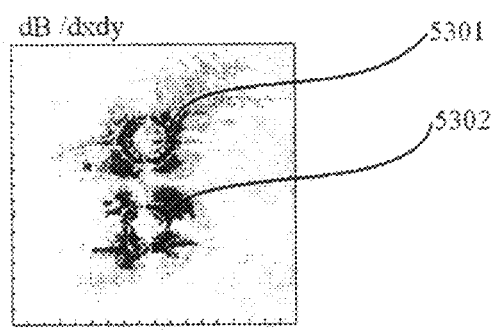

In FIG. 6A, plane coordinates indicate surface positions of an object to be measured, and vertical coordinates indicate the amplitude B of an AC magnetic field in each of the surface positions. FIG. 6B illustrates a differential value (dB/dx) of the amplitude B of the AC magnetic field with respect to a horizontal direction of a surface current, FIG. 6C illustrates a differential value (dB/dy) of the amplitude B of the AC magnetic field with respect to a vertical direction of the surface current, and FIG. 6D illustrates a differential value (dB^2/dxdy) of the amplitude B with respect to horizontal and vertical direct ions of the surface current.

FIGS. 6A through 6D illustrates end positions 5001 and 5002, 5101 and 5102, 5201 and 5202, and 5301 and 5302 of a crack, and a distance 6001 between two centers of end positions, wherein the distance corresponds to a length of a crack. A diameter 6002 shown in FIG. 6B corresponds to the width of the crack, and a means of maximum values 6003 shown in FIG. 6A corresponds to the depth of the crack.

FIGS. 7A through 7D illustrate the detection results of FIG. 6 that are quantitatively analyzed.

As shown in FIGS. 7A through 7D, the substantial size of crack is quantitatively analyzed based on the distance 6001, the diameter 6002, and the means of maximum values 6003.

Figure 7A:
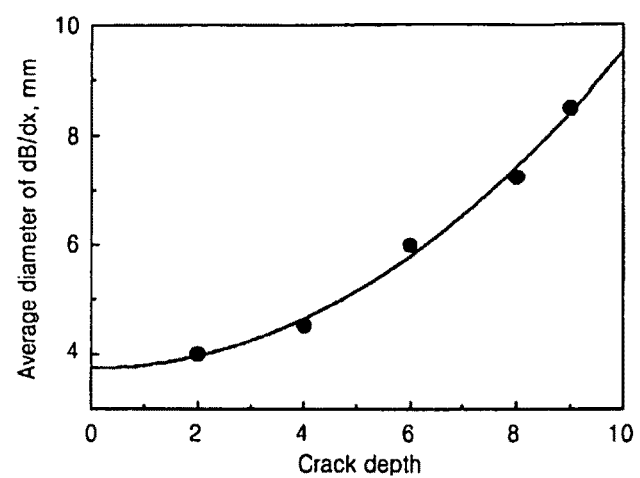
FIGS. 7A through 7D illustrate the detection results of FIG. 6, which are quantitatively analyzed.
Figure 7B:
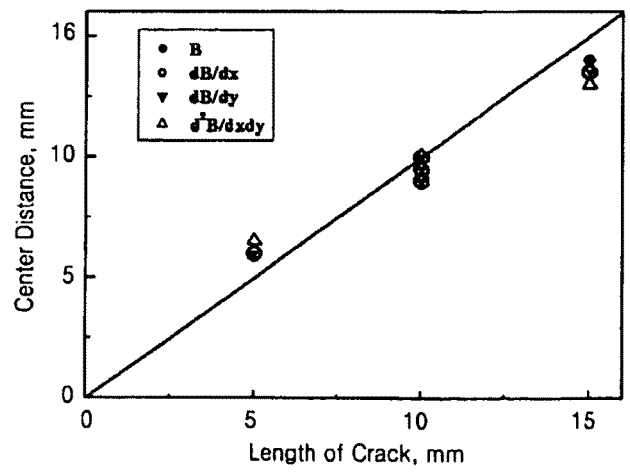
Figure 7C:
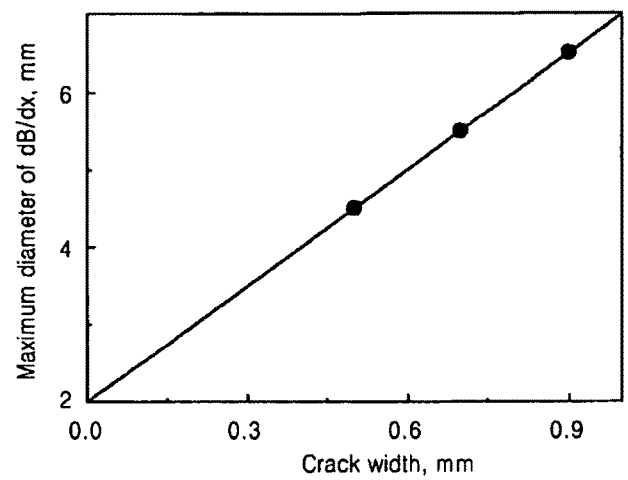
Figure 7D:
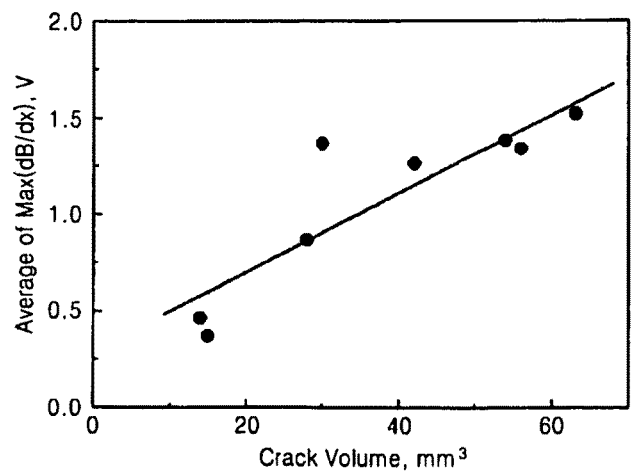

As shown in FIG. 7A, a crack depth is measured from an average diameter of the differential value (dB/dx) of the amplitude B with respect to the horizontal direction of the surface current. As shown in FIG. 7B, the length of a crack is measured from a center distance between two centers of end positions. As shown in FIG. 7C, a crack width is measured from a maximum diameter of the differential value (dB/dx) of the amplitude B with respect to the horizontal direction of the surface current. As shown in FIG. 7D, a crack volume is measured from an average of a maximum value of the differential value (dB/dx) of the amplitude B with respect to the horizontal direction of the surface current.

Figure 8A:
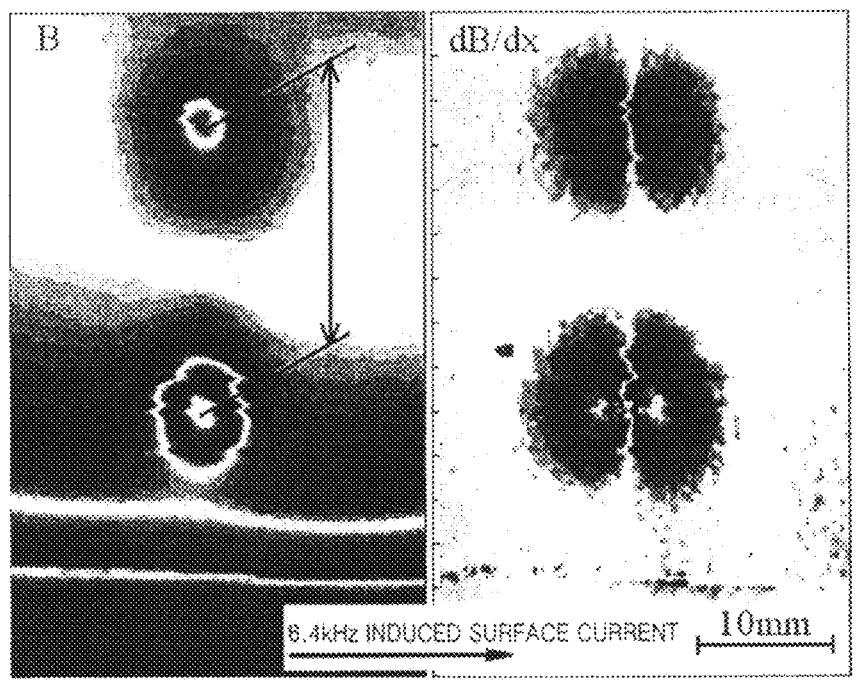
FIG. 8A illustrates surface cracks of a paramagnetic structure (aluminum alloy) detected using a defect detection apparatus of the present invention.
Figure 8B:
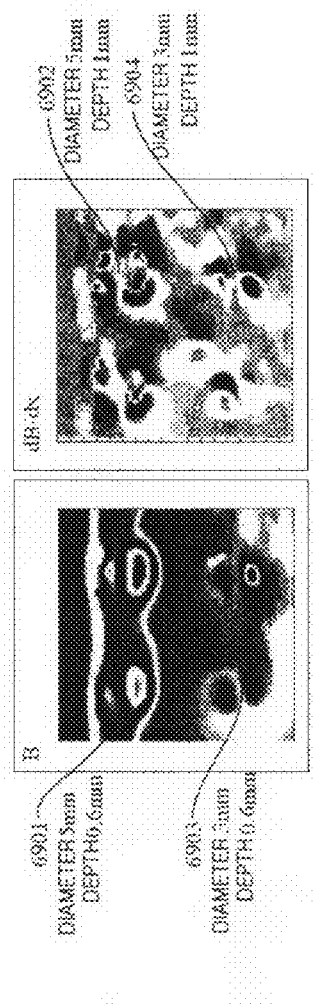
FIG. 8B illustrates surface cracks of a ferromagnetic structure (carbon steel) detected using the defect detection apparatus of the present invention.

FIG. 8A illustrates a surface crack of a paramagnetic structure (aluminum alloy) that are detected using a defect detection apparatus of the present invention. FIG. 8B illustrates a surface crack of a ferromagnetic structure (carbon steel) that are detected using the defect detection apparatus of the present invention.

As described above, a defect detection apparatus according to the present invention can detect cracks of an object that is to be measured, wherein ferromagnetic and paramagnetic substances are mixed in the object. Also, the defect detection apparatus can detect a crack of the paramagnetic structure as illustrated in FIG. 8A and a crack of the ferromagnetic structure as illustrated in FIG. 8B.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:
1. An apparatus for detecting a defect, comprising:
an induced current applier applying surface currents to an object that is to be measured by using ACs (alternating currents) having a frequency varying depending on a depth to be measured;
a magneto-electric converter sensing a magnetic field generated from the object due to the surface currents and generating a magnetic field sensing signal corresponding to a strength of the magnetic field;
a signal processor filtering and amplifying the magnetic field sensing signal and outputting a signal corresponding to an amplitude of the filtered and amplified magnetic field sensing signal;
a signal converter converting the signal output from the signal processor into a digital signal; and
a data processor quantitatively converting the strength of the magnetic field generated from the object into a numerical value based on the digital signal output from the signal converter,
wherein the induced current applier comprises
an AC power supplier generating the ACs;
at least one first coil transmitting the ACs;
at least one core on which the first coil is wound, and the core in which a varying magnetic field is induced by the ACs; and
at least one conductive plate in which the surface currents are induced by the varying magnetic field, and the at least one conductive plate applying the surface currents to the object,
wherein the data processor calculates an amplitude of the magnetic field generated from each position of the object, a differential value dB/dx of the amplitude of the magnetic field with respect to a horizontal direction of induced currents in the object, a differential value dB/dy of the amplitude of the magnetic field with respect to a vertical direction of the induced currents, and a differential value dB^2/dxdy of the amplitude of the magnetic field with respect to horizontal and the vertical directions converts the amplitude of the magnetic field and the differential values of the amplitude of the magnetic field into numerical values, and quantitatively analyzes defects of the object,
wherein the at least one conductive plate consists of a plurality of plates, the plurality of plates are linked so as to form loop, and one of the plurality of plates is adhered to the object,
wherein B is the amplitude of the magnetic field, x is displacement of the horizontal direction of the induced currents, and y is displacement of the vertical direction of the induced currents.

2. The apparatus of claim 1, wherein the at least one first coil, the at least one core and the at least one conductive plate are respectively a plurality of first coils, a plurality of cores and the plurality of plates, and the induced current applier further comprises a divider distributing the ACs to the plurality of first coils.

3. The apparatus of claim 2, wherein the divider controls phases of the ACs that are distributed to the plurality of first coils, and the plurality of conductive plates are orthogonal to one another.

4. The apparatus of claim 1, wherein the at least one core comprises a plurality of through paths through which the at least one conductive plate penetrates so as to strengthen the surface currents that is applied to the object.

5. The apparatus of claim 1, wherein the magneto-electric converter comprises hall sensors arrayed in M rows and N lines, magneto-resistive sensors arrayed in M rows and N lines, or giant magneto-resistive sensors arrayed in M rows and N lines, wherein the hall sensors, the magneto-resistive sensors, or the giant magneto-resistive sensors are arrayed on one of 2-dimensional plane and 3-dimensional curved surface.

6. The apparatus of claim 1, wherein the magneto-electric converter comprises hall sensors arrayed in M rows and N lines, M first power lines, M second power lines, and first output lines,
  wherein first power terminals of the hall sensors in one row among the M rows are commonly connected to one of the first power lines in the one row, second power terminals of the hall sensors in the one row are commonly connected to one of the second power lines in the one row, and first output terminals of the hall sensors in one line among the N lines are commonly connected to one of the first output lines in the one line.

7. The apparatus of claim 6, wherein when a first power source is applied to the first power lines and a ground is connected to the second power lines, one of the hall sensors outputs the magnetic field sensing signal corresponding to the strength of the magnetic field, which is generated from the object and incident onto the one of the hall sensors, through one of the first output lines connected to the one of the hall sensors.

8. The apparatus of claim 7, wherein when the one of the hall sensors outputs the magnetic field sensing signal through the one of the first output lines, a second output terminal of the one of the hall sensors is in floating state or grounded.

9. The apparatus of claim 6, wherein the magneto-electric converter further comprises second output lines, wherein second output terminals of the hall sensors in the one line are commonly connected to one of the second output lines in the one line.

10. The apparatus of claim 9, wherein when a first power source is applied to the first power lines and a ground is connected to the second power lines, one of the hall sensors outputs the magnetic field sensing signal corresponding to the strength of the magnetic field, which is generated from the object and incident onto the one of the hall sensors, through one of the first output lines and one of the second output lines connected to the one of the hall sensors.

11. The apparatus of claim 6, wherein the magneto-electric converter further comprises resistors arrayed in the M rows and N lines, wherein each of the first power terminals of the hall sensors are connected to the first power lines through their own respective resistor.

12. The apparatus of claim 1, wherein the magneto-electric converter comprises:
  a hall effect material coated on a substrate and having a predetermined size;
  M first power terminals formed on a first side of the hall effect material;
  M first power switches respectively connected to the M first power terminals;
  M second power terminals formed on a second side of the hall effect material;
  M second power switches respectively connected to the M second power terminals;
  N first output terminals formed on a third side of the hall effect material; and
  N second output terminals formed on a fourth side of the hall effect material.

13. The apparatus of claim 1, wherein the signal processor comprises:
  a high-pass filter removing a component of DC magnetic field formed by a ferromagnetic substance in the object from the magnetic field sensing signal;
  an amplifier amplifying and outputting the magnetic field sensing signal from which the component of DC magnetic field is removed; and
  a smoothing circuit outputting the signal corresponding to the amplitude of the filtered and amplified magnetic field sensing signal.

14. The apparatus of claim 13, wherein the smoothing circuit is one of an RMS (root mean square) circuit, a lock-in-amplifier, and a maximum value detecting circuit.

* * * * *